United States Patent [19]

Marken

[11] Patent Number: 4,875,718

[45] Date of Patent: Oct. 24, 1989

[54] SWIVEL CONNECTOR FOR PREVENTING KINKING OF FLEXIBLE MEDICAL HOSES

[76] Inventor: Robert E. Marken, 21495 Bear Creek Rd., Bend, Oreg. 97701

[21] Appl. No.: 279,048

[22] Filed: Dec. 2, 1988

[51] Int. Cl.⁴ .................. A61M 15/00; F16L 27/04; F16L 31/00; F16L 47/00

[52] U.S. Cl. ......................... 285/175; 128/912; 285/261; 285/310; 604/905

[58] Field of Search ............. 285/261, 262, 160, 166, 285/167, 169, 260, 238, 175; 128/912; 604/905

[56] References Cited

U.S. PATENT DOCUMENTS

| | | | |
|---|---|---|---|
| 2,366,067 | 12/1944 | Smith | 285/260 X |
| 3,431,370 | 3/1969 | Crosby | 285/261 X |
| 3,548,827 | 12/1970 | Abel | 128/275 |
| 4,004,586 | 1/1977 | Christensen | 285/260 X |
| 4,056,116 | 11/1977 | Carter | 604/905 X |
| 4,084,843 | 4/1978 | Gassert | 285/340 X |
| 4,146,254 | 3/1979 | Turner | 285/340 X |
| 4,676,241 | 6/1987 | Webb | 128/207.14 |
| 4,686,977 | 8/1987 | Cosma | 128/207.14 |
| 4,773,680 | 9/1988 | Krumme | 285/340 X |
| 4,778,447 | 10/1988 | Velde | 604/905 X |

FOREIGN PATENT DOCUMENTS

| | | | |
|---|---|---|---|
| 2448426 | 4/1975 | Fed. Rep. of Germany | 285/261 |
| 0615317 | 1/1961 | Italy | 285/261 |

Primary Examiner—Randolph A. Reese
Assistant Examiner—Paul M. Frechette
Attorney, Agent, or Firm—Terry M. Gernstein

[57] ABSTRACT

A swivel connector in the form of a ball and socket joint is used to connect flexible hoses that are used in a medical treatment, such as an oxygen hose, to prevent such hoses becoming kinked when an ambulant patient moves about. The connector can be formed of autoclavable material, and several such connectors can be included in one fluid system. The connector includes a ball member assembly and a socket member assembly, with a gland in the socket member assembly for engaging one of the hoses in a fluid-tight manner forming a fluid-tight chamber in the connector.

5 Claims, 1 Drawing Sheet

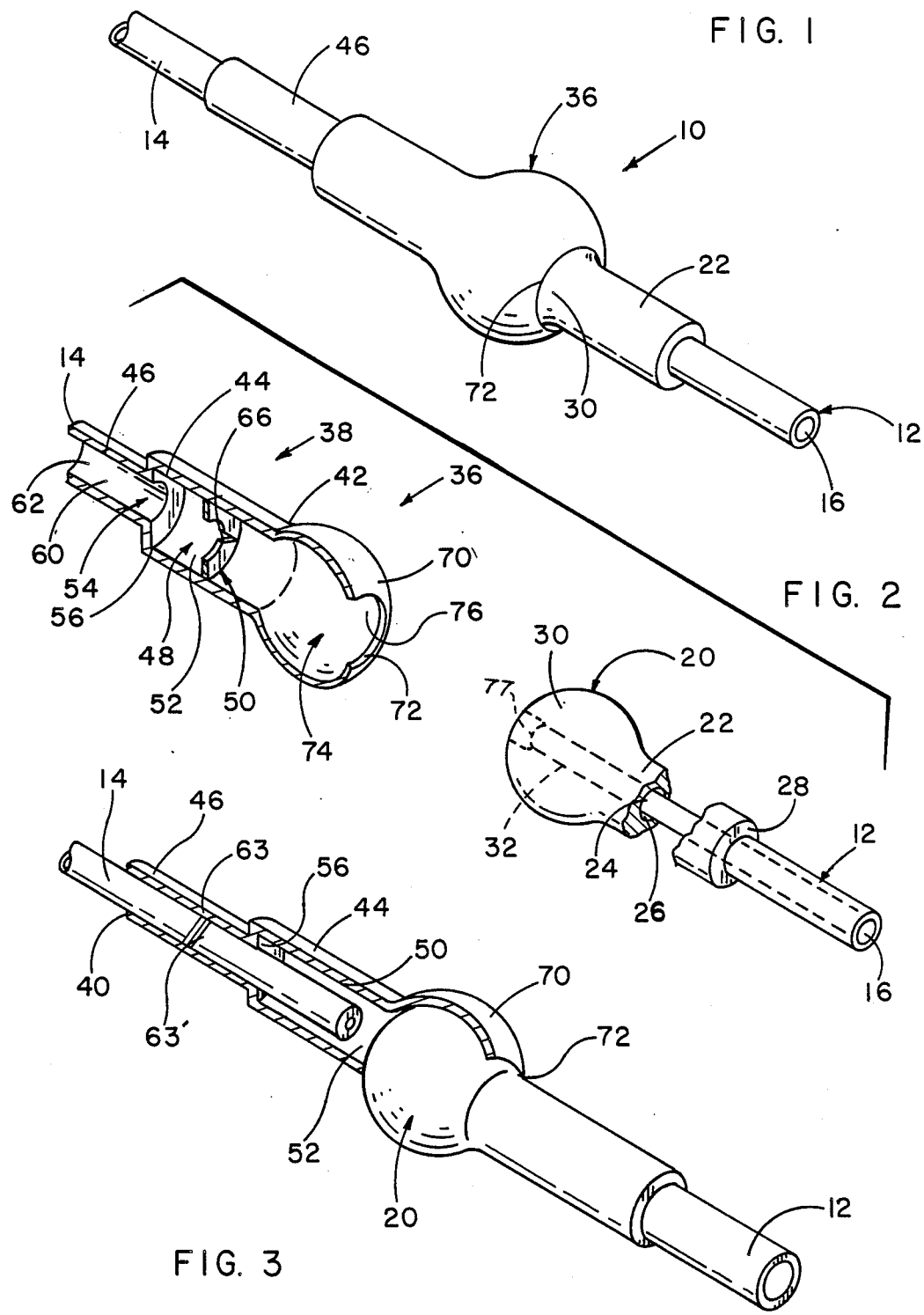

4,875,718

SWIVEL CONNECTOR FOR PREVENTING KINKING OF FLEXIBLE MEDICAL HOSES

TECHNICAL FIELD OF THE INVENTION

The present invention relates to the general field of connectors, and to the particular field of hose connectors. Specifically, the present invention relates to a hose connector for use in the medical field which permits the connected hoses to swivel with respect to each other without kinking.

BACKGROUND OF THE INVENTION

Ambulation is quite common in modern medical treatment regimens. It is quite common for a patient who has undergone major surgery to be strongly encouraged to get out of bed and walk as much as possible as soon as possible.

However, many such patients require catheterization, or IV set-ups. Therefore, such ambulation, while extremely desirable, may be difficult due to the need for such tubes as are associated with catheters, IV's and the like. It is not uncommon in a hospital to see a patient walking with tubes attaching him to bottles and containers supported on a stand or cart that must be pulled or pushed along with such patient as he walks. Unless caution is exercised, these tubes can become kinked thereby causing the patient discomfort and possibly interfering with the operation of the fluid systems associated with the kinked tube. This clearly is an undesirable situation and patients and health care professionals must be constantly aware of the tubes to avoid such a situation.

While the kinking of catheter and IV tubes is quite undesirable, and potentially harmful, the kinking of an oxygen tube is totally unacceptable. Many patients, both ambulatory and bedridden, require oxygen, and such oxygen is provided via flexible tubes and hoses. An ambulatory patient may cause the oxygen hose to kink, and even a bedridden patient who occasionally moves can create an oxygen-hose kinking situation. The more active the patient, the greater the possibility of oxygen-hose kinking situations arising.

The just-mentioned situation is exacerbated by patients who are otherwise well, but who suffer from some respiratory problem, such as emphysema or the like, that requires an otherwise well and mobile patient to have oxygen-hoses. Such a patient is quite active and the potential for an oxygen-hose kinking situation is concomitantly increased. Such people often are required to pull the hoses over their heads to untwist such hoses, an obviously undesirable situation.

Accordingly, there is need for a device that is adapted for use with medical fluid systems, such as oxygen-supply systems, and which prevents, or at least, inhibits, the flexible hoses associated with such systems from kinking.

OBJECTS OF THE INVENTION

It is a main object of the present invention to provide a hose connector that prevents medical hoses from kinking.

It is a another object of the present invention to provide a hose connector that prevent medical hoses from kinking while being easy and inexpensive to manufacture.

It is a another object of the present invention to provide a hose connector that prevents medical hoses from kinking that is adaptable for use on long hoses and in multiples.

SUMMARY OF THE INVENTION

These, and other, objects are accomplished by a ball and socket connector that has means for securely retaining a hose in both the ball member assembly of the connector and in the socket member assembly of the connector. The connector also includes a gland which prevents the leakage of fluid, such as oxygen, from the connector.

The ball member assembly includes a ball which is joined to a socket member of the socket member assembly so that relative movement is permitted in all planes.

In this manner, line kinking is prevented since the hoses, or the sections of the same hose, that are connected by the connector can move relative to each other in all planes. The range of the angular movement permitted is determined only by the design and relative proportions of the members. Due to the fluid tight nature of the connector, even though a large amount of relative movement is permitted, fluid leakage will not occur.

BRIEF DESCRIPTION OF THE FIGURES

FIG. 1 is a perspective of the device.

FIG. 2 is an exploded, partially cutaway perspective of the device showing one hose connected thereto.

FIG. 3 is a partially cutaway perspective of the device showing two hoses connected thereto to be fluidically joined and universally movable with respect to each other.

DETAILED DESCRIPTION OF THE PREFERRED EMBODIMENT

Shown in FIG. 1 is a swivel connector 10 of the ball and socket joint type for connecting hose portions 12 and 14 together. The hose portions 12 and 14 can be different hoses or can be sections of the same hose that has been separated to accommodate the connector 10. The connector 10 permits the hoses to move with respect to each other in all planes and through a wide range of angles whereby the hoses 12 and 14 will be inhibited from winding together or about themselves in a kinking fashion. For the purposes of this disclosure, a "kink" is a tightened loop in a hose.

The hose sections are tubular in nature and each has a central longitudinally extending bore, such as bore 16 in hose 12, through which fluid, such as oxygen, flows during the carrying out of a medical procedure. The connector 10 connects the hoses 12 and 14 together in a fluid-tight manner so that fluid will flow smoothly from hose 12 to hose 14 (or vice versa) without leakage occurring at the connection of those two hoses. As will occur to those skilled in the art, a kinking of either or both of the hoses may inhibit or prevent the passage of fluid through either or both of the hoses.

As is best shown in FIGS. 1 and 2, the connector 10 includes a ball member assembly 20. The ball member assembly 20 includes a sleeve 22 having a bore 24 defined therethrough for accommodating the first hose 12 therein with the bores 16 and 24 being co-axially arranged. The ball member assembly sleeve 22 includes a hose retaining means, such as projections 26, for securely holding the first hose 12 in the sleeve bore 24. Other hose retaining means can be used without departing from the scope of the present disclosure. The sleeve 22 has an axial extent that is selected to securely hold the hose 12 in place without being so long as to inhibit movement of that hose.

The sleeve 22 has a distal end 28 and a proximal end to which a ball 30 is affixed. The ball 30 includes a bore 32 extending diametrically therethrough for accommodating the first hose 12. The hose 12 can terminate within the bore 32 as is indicated in FIG. 2, or extend slightly out of such bore. However, as will be apparent from the ensuing discussion, if the hose 12 extends out of the bore 32, it might interfere with the movement of the connector 10.

As is also shown in FIGS. 1 and 2, the connector 10 includes a socket member assembly 36. The socket member assembly 36 includes a sleeve 38 having a distal end 40 and a proximal end 42 adapted to be located on the second hose 14 so the connector will support the second hose 14 without interfering with the overall operation of the connector.

As is best shown in FIGS. 2 and 3, the sleeve 38 includes a first portion 44 located adjacent to the sleeve proximal end 42 and a second portion 46 located adjacent to the sleeve distal end 40. Both of the portions 44 and 46 are tubular and the diameter of the second portion 46 is smaller than the diameter of the first portion 44 so that a stepped shape is defined.

The first portion 44 includes a central bore 48 extending longitudinally from the proximal end 42 and having a gland 50 located therein and mounted on inner surface 52 of the first portion. The gland 50 will be described in greater detail below.

The sleeve second portion 46 includes a bore 54 extending longitudinally thereof from the distal end 40 and having the longitudinal centerline thereof aligned with the longitudinal centerline of the first sleeve portion 44. The bores 48 and 54 are tubular and the second bore 54 has a diameter that is smaller than the diameter of the first bore 48 so a shoulder 56 is defined at the intersection of the two bores 48 and 54. The diameter of the bore 54 is sized to be approximately the same as the outer diameter of the second hose 14 to snugly accommodate such hose as shown in FIGS. 1 and 3.

A second hose retaining means, such as projections 60, is mounted on inner surface 62 of the second bore 54 to securely retain the second hose 14 in the sleeve 38.

Other forms of the retaining means can be used, such as a coupling thread-forming element on the inner surface of one or both of the sleeves which defines a cooperating thread in the soft flexible hose associated with such sleeve. An example of such thread-forming element is indicated in FIG. 3 by the reference indicator 63. The element 63 can be a screw thread on surface 62 of sleeve 38 which defines co-operating screw thread 63' in the outer surface of second hose 14 when the hose is inserted into the sleeve. It may be necessary to rotate the hose 14 with respect to the sleeve upon such insertion to define such screw threads 63'. Similar thread-forming means can be used on the sleeve 22.

The gland 50 is annular and is firmly affixed to the inner surface 52 of the sleeve first portion 44. The annular opening of the gland is sized to snugly and securely hold and support the second hose 14 as is indicated in FIG. 3. The gland is sized to surround the second hose 14 in a fluid tight manner to prevent leakage from the connector 10. The gland 50 can be formed of a plastics-type material, or can be rubber or the like as will occur to those skilled in the art based on the disclosure herein. The gland 50 can serve to support the hose 14 if suitable and can be flexible enough to permit the hose to move into the FIG. 3 position, while being designed to prevent backsliding of the hose 14 from the FIG. 3 position. Cutout portions, such as cutout portion 66 shown in FIG. 2 can be defined to permit such one-way grasping of the hose by the gland.

As can be seen by comparing the Figures, the hoses 12 and 14 are fluidically connected together by the connector 10 so that the terminal ends of the hoses are in end-to-end confronting relationship within a fluid-tight cavity.

As is shown in the Figures, the socket member assembly 36 further includes a socket 70 mounted on the proximal end 42 of the sleeve 38. The socket 70 is sized and designed to accommodate the ball 30 in a swiveling manner, and includes a hole 72 defined at one location to fit around the sleeve 22 of the ball member assembly in a manner that permits the ball to swivel with respect to the socket 70. The socket 70 is attached to the sleeve 38 at its proximal end at a location diametrically opposite to the hole 72 whereby a cavity 74 is defined by the inner surface 76 of the socket 70. The cavity 74 is sized to accommodate the ball 30 in a manner that permits the desired swiveling of the ball member assembly with respect to the socket member assembly.

As can be seen from FIG. 2, if the terminal end 77 of first hose 12 were to extend out of the ball 30, such end 77 might contact the inner surface 52 of the sleeve portion 44 in some configurations of the connector and thus interfere with the overall operation of such connector. Accordingly, it is preferred that the hose terminal end 77 be located within the outer perimeter of the ball 30 as shown in FIG. 2. However, if the inner diameter of the sleeve portion 44 is selected to be large enough, this terminal end can extend out of the ball.

The connector 10 thus defined permits the hoses 12 and 14 to move with respect to each other in the manner of a ball and socket joint, but which also has a fluid-tight seal defined therein.

The operation of the connector is evident from the figures and from the foregoing description, and thus will not be specifically discussed. However, those skilled in the art will be able to see that the ball assembly member 20 will attach to the first hose 12 and the socket member assembly 36 will attach to the second hose 14, and the ball 30 of the member 20 will be received in the socket 70 in a manner of a ball and socket joint to permit the hoses 12 and 14 to swivel with respect to each other to prevent kinking of either or both hoses either to itself or to the other hose.

Since the connector 10 can be used in a medical environment, it should be manufactured from an autoclavable material.

As above mentioned, the hoses 12 and 14 can be separate or can be sections of the same hose that has been divided to place the connector therein.

Still further, the connector 10 can be placed adjacent to a supply valve of a fluid container, such as an oxygen source and be used to connect the hose to such supply valve. Still further, several connectors can be inserted into a hose that is quite long.

While the connector 10 has been disclosed as being useful in an oxygen hose, it could be used in other medical situations as well without departing from the scope of the present invention. For example, the connector could be used in a liquid transfer set-up or in other set-ups for gases other than oxygen.

A plurality of glands 50 can also be used to further ensure the fluid-tightness of the connector and to further ensure the secure support of the hose 14. For example, the several glands could be located in the bore 48 and be spaced apart along the longitudinal axis of that bore.

It is to be understood that while certain forms of the present invention have been illustrated and described herein, it is not to be limited to the specific forms or arrangement of parts described and shown.

I claim:

1. A swivel connector for preventing the kinking of a fluid hose, such as an oxygen hose, comprising:
 (A) a ball member assembly which includes
  (i) a first hose having an end, a sleeve having a bore defined therethrough for accommodating said first hose, said first hose end being located in said ball member assembly,
  (ii) a hose retaining means in said sleeve securely holding said first hose in place in said sleeve,
  (iii) a ball affixed to one end of said sleeve and spaced from said hose retaining means and having a bore defined diametrically therethrough to have ends defined in an outer surface of said ball, said ball bore being aligned with and fluidically joined to said sleeve bore and being sized to accommodate said first hose therethrough, said first hose being mounted in said sleeve by said hose retaining means to extend through one of said bore ends and to have said hose end spaced from another end of said bore and located inside said ball bore; and
 (B) a socket member assembly which includes
  (i) a second hose having an end, and a sleeve having
   (a) a first portion with a bore defined therethrough, an annular hose supporting gland mounted in said sleeve first portion to accommodate and grasp said second hose, said second hose end being located in said first portion, said annular gland having a cutout portion defined therein and having an annular opening that is sized so that said second hose is permitted to move therethrough in one direction while said gland prevents said second hose from backsliding therethrough in a second direction that is opposite to said one direction,
   (b) a sleeve second portion with a bore defined therethrough, said sleeve second portion having an inner diameter that is approximately the same as the outer diameter of said second hose to snugly accommodate said second hose and being smaller in diameter than said first sleeve portion bore, and being joined to one end of said first sleeve portion to define a shoulder, with said annular gland being spaced from said shoulder,
   (c) a second hose retaining means in said sleeve second portion holding said second hose in said sleeve second portion, and
  (ii) a socket mounted on one end of said second sleeve first portion and having a hole defined therein which is sized to be larger than said ball member assembly sleeve and located to accommodate said ball member assembly sleeve when said ball is received in said socket, said socket being sized to essentially completely surround said ball;
 (C) said second hose retaining means holding said second hose in a position that has the end of said second hose spaced from said socket, with said sleeve second portion being larger than said second hose, said second sleeve, said gland and said ball forming a chamber in which said second hose end is located.

2. The connector defined in claim 1 wherein socket member assembly first portion is sized to accommodate the first and second hoses in end-to-end confronting relation.

3. The connector defined in claim 2 wherein said connector is formed of autoclavable material.

4. The connector defined in claim 3 wherein said first hose retaining means includes projections on the inner surface of said ball member assembly sleeve.

5. The connector defined in claim 1 wherein said second hose retaining means includes a screw thread-forming means on said sleeve second portion.

* * * * *